(12) United States Patent
Heuer

(10) Patent No.: US 8,519,193 B2
(45) Date of Patent: Aug. 27, 2013

(54) DIALKYL PHENOLS

(75) Inventor: Lutz Heuer, Dormagen (DE)

(73) Assignee: LANXESS Deutschland GmbH, Leverkusen (DE)

( * ) Notice: Subject to any disclaimer, the term of this patent is extended or adjusted under 35 U.S.C. 154(b) by 182 days.

(21) Appl. No.: 12/669,976

(22) PCT Filed: Jul. 15, 2008

(86) PCT No.: PCT/EP2008/059217

§ 371 (c)(1), (2), (4) Date: Sep. 17, 2010

(87) PCT Pub. No.: WO2009/016028

PCT Pub. Date: Feb. 5, 2009

(65) Prior Publication Data

US 2010/0331579 A1 Dec. 30, 2010

(30) Foreign Application Priority Data

Jul. 28, 2007 (DE) .......................... 10 2007 035 515

(51) Int. Cl.
*C07C 37/74* (2006.01)

(52) U.S. Cl.
USPC .............................. 568/343; 568/345; 568/756

(58) Field of Classification Search
USPC .................................................. 568/343, 345
See application file for complete search history.

(56) References Cited

U.S. PATENT DOCUMENTS

| 1,886,311 A | 11/1932 | Skraup et al. |
| 2,468,670 A | 4/1949 | Huggett et al. |
| 2,603,662 A | 7/1952 | Stevens |
| 3,331,879 A | 7/1967 | Leston |
| 3,992,455 A | 11/1976 | Leston |
| 4,086,283 A | 4/1978 | Biedermann et al. |
| 5,030,770 A | 7/1991 | Wimmer et al. |

FOREIGN PATENT DOCUMENTS

| GB | 285833 A | 5/1929 |
| GB | 1227924 A | 4/1971 |
| GB | 1344965 | 1/1974 |
| JP | 60139636 | 7/1985 |

*Primary Examiner* — Sikarl Witherspoon
(74) *Attorney, Agent, or Firm* — Michael A. Miller

(57) ABSTRACT

The present invention relates to a method for producing 4-isopropyl-3-methyl-phenol by alykylizing meta-cresol, distilling, and crystallizing.

7 Claims, No Drawings

DIALKYL PHENOLS

The present invention relates to a process for preparing 4-isopropyl-3-methylphenol by alkylation of meta-cresol, distillation, and crystallization.

4-Isopropyl-3-methylphenol is used, for example, as an antibacterial and microbicidal agent in cosmetics, mouthwashes, and shampoos which are highly skin-friendly. The preparation of 4-isopropyl-3-methylphenol is known in principle.

Thus U.S. Pat. No. 3,331,879 describes the reaction of meta-cresol (m-cresol, 3-methylphenol) with propene over a zirconium catalyst to give substantially thymol (2-isopropyl-5-methylphenol) but also numerous aromatic byproducts. One byproduct identified was 4-isopropyl-3-methylphenol, present at 2% in the reaction mixture or at 4.4% following a first distillation. Isolation of the 4-isopropyl-3-methylphenol is not described.

DE 2139622 A describes the formation of up to 19.5% of 4-isopropyl-3-methylphenol in the reaction of m-cresol with propene over an acidic zinc catalyst. Here again, isolation of the 4-isopropyl-3-methylphenol is not described.

DE 2528303 A describes the formation of around 2% of 4-isopropyl-3-methylphenol in the reaction of meta-cresol with propene over a basic alumina catalyst. Isolation of the 4-isopropyl-3-methylphenol from the multifarious byproducts is not described.

Moreover, it is known from U.S. Pat. No. 2,603,662 to obtain 4-isopropyl-3-methylphenol via a costly and complicated operation, as a byproduct in the reaction of meta-cresol with isobutene.

Common to all of the aforementioned processes is the formation of 4-isopropyl-3-methylphenol as a by-component in the alkylation of m-cresol, along with so many other by-components that its recovery either was not performed or is extraordinarily awkward. The need existed, therefore, to provide a process allowing 4-isopropyl-3-methylphenol to be obtained efficiently.

A process has now been found for preparing 4-isopropyl-3-methylphenol by reaction of meta-cresol with propene, which is characterized in that
  a) thymol and unreacted meta-cresol are largely removed distillatively from the reaction mixture and
  b) the residue remaining from step a) is then distilled in order to remove extremely unvolatile or nonvolatile substances and the resulting distillate, optionally after addition of up to 5% by weight of water, is crystallized, or
  c) the residue remaining from step a), optionally after addition of up to 5% by weight of water, is crystallized and the crystallized residue is separated by distillation from extremely unvolatile or nonvolatile substances.

The scope of the invention encompasses not only the stated ranges and preference ranges of formulae and parameters but also any desired combinations, even if not explicitly and completely set out below, for practical reasons.

The alkylation of meta-cresol with propene, which can be carried out in a manner which is known to the skilled worker (see, for example, DE 3824284 A or DE 2528303 A), typically produces a reaction mixture containing approximately 1% to 3% by weight of 4-isopropyl-3-methylphenol.

In one step a) of the process of the invention, thymol and unreacted meta-cresol are largely removed distillatively from the reaction mixture. The epithet "largely" here means that the residue which remains has a combined thymol and meta-cresol content totaling 80% or less, preferably 55% or less and more preferably 20% or less.

This distillation can be carried out in a conventional manner, for example, discontinuously or continuously, with preference being given to a continuous distillation under a pressure which is reduced relative to atmospheric pressure.

The residue which remains typically comprises not only 4-isopropyl-3-methylphenol but also 20 to 30 other by-components of low-molecular structure, and polymeric by-components as well. Following the distillation, the amount of 4-isopropyl-3-methylphenol in the residue which remains, and which is typically of a black coloration, is customarily 10% to 30% by weight.

In accordance with step b), the residue which remains from step a) can first of all be distilled in order to remove extremely unvolatile or nonvolatile substances, and the resulting distillate, optionally after addition of up to 5% by weight of water, can be crystallized.

As an alternative to this, in accordance with step c), the residue which remains from step a) can be crystallized and the crystallized residue can be separated by distillation from extremely unvolatile or nonvolatile substances.

The distillation in step b) or c) may take place in a conventional way, for example, continuously or discontinuously. The distillation takes place preferably with the aid of a short-path evaporator, a column without internals, or a falling-film evaporator or else a thin-film evaporator. One theoretical plate is sufficient for the distillation.

Suitable distillation conditions can be determined readily by the skilled worker.

In one embodiment of the process of the invention the distillations of steps a) and b) can also be carried out simultaneously. Preference is given in this case to distillation in a side stream takeoff column.

In accordance with step b) the distillate is crystallized and in accordance with step c) the residue remaining from step a) is crystallized. The crystallization in these cases may take place, for example, at temperatures of −50 to 80° C. The crystallization takes place preferably at temperatures of 0 to 50° C., more preferably at temperatures of 5 to 35° C.

In one embodiment of the invention the distillate as per step b) or the residue which remains from step a) is admixed with water, preferably with 0.01% to 5% by weight, based on the weight of the distillate, more preferably 1% to 5% by weight.

In another embodiment the crystallization takes place such that the distillate as per step b) or the residue which remains from step a) is admixed with crystalline 4-isopropyl-3-methylphenol, preferably with a few crystals. This crystallization may take place continuously or discontinuously. On standing, preferably for 2 to 200 hours, a crystal cake is formed from which it is possible by decanting to obtain 4-isopropyl-3-methylphenol with a typical purity of 85% to 95%, based on the weight. Surprisingly, the crystallization can take place without solvent or diluent, even though the other substances of the residue from step a) or of the distillate as per step b) are also solids. Examples thereof are 2-isopropyl-5-methylphenol, with a melting point of 49° C., 3-methylphenol with a melting point of 12° C., and 3-isopropyl-5-methylphenol, with a melting point of 49 to 51° C.

The crystalline 4-isopropyl-3-methylphenol obtained in accordance with step b) or c) can be purified further by washing with a $C_1$ to $C_4$ alcohol, with mixtures of such alcohols or with mixtures of one or more of these alcohols with water. Preferred $C_1$ to $C_4$ alcohols are methanol, ethanol, and isopropanol. In mixtures with water, the water fraction is for example 1% to 90% by weight, preferably 40% to 90% by weight.

For a further increase in purity it is also possible to recrystallize the inventively obtainable 4-isopropyl-3-methylphenol. Preferred solvents for the recrystallization are the $C_1$ to $C_4$ alcohols stated above, mixtures of such alcohols, or mixtures of one or more of these alcohols with water. The recrystallization takes place preferably with addition of filtration aids or activated carbon.

In another embodiment the crystallization may take place such that the crystallization takes place continuously or discontinuously as a result of cooling. The cooling takes place preferably on a tube, tube bundle or container coolable by other internals, this apparatus being cooled in comparison to the ambient temperature, and the resultant crystals, after the other compounds have been drained off, are melted off by heating of the tube, tube bundle or other containers coolable by internals. This operation is preferably repeated, giving highly pure 4-isopropyl-3-methylphenol.

In the process regime in accordance with steps a) and c) it is advantageous that, with the same operations, highly pure 4-isopropyl-3-methylphenol can be obtained.

The particular advantage of the invention is to be seen in the fact that 4-isopropyl-3-methylphenol can be obtained efficiently and in high purity, as a by-component in thymol preparation in spite of the presence of a very large number of further by-components which are likewise solid at room temperature.

EXAMPLE

At 150° C. and 1 mbar, 1000 g of black residue from thymol preparation, containing 18.5% by weight thymol, 9.5% by weight 3-isopropyl-5-methylphenol, 26.2% by weight 4-isopropyl-3-methylphenol, 16.5% by weight 2,6-diisopropyl-3-methylphenol, 24.2% by weight 2,4-diisopropyl-5-methylphenol, and about 22 different other alkylated cresols, totaling around 5% by weight, were distilled using a Claissen attachment without column. This gave 993.3 g of a yellowish distillate of approximately the above composition. Of this oil, 200 g were seeded at 22° C. with 0.4 g of pure crystalline 4-isopropyl-3-methylphenol in suspension in 3 ml of water. After 48 h, 40.2 g (76.7% of theory) of colorless crystals of 4-isopropyl-3-methylphenol were obtained, and, after washing with a little methanol, they had a purity of 95.1%.

What is claimed is:

1. A process for preparing 4-isopropyl-3-methylphenol by reacting meta-cresol with propene, characterized in that
   a) thymol and unreacted meta-cresol are largely removed distillatively from the reaction mixture and
   b) the residue remaining from step a) is then distilled in order to remove extremely unvolatile or nonvolatile substances and the resulting distillate, after addition of up to 5% by weight of water, is crystallized, or
   c) the residue remaining from step a), after addition of up to 5% by weight of water, is crystallized and the crystallized residue is separated by distillation from extremely unvolatile or nonvolatile substances.

2. The process of claim 1, characterized in that the distillations of steps a) and b) are carried out simultaneously.

3. The process of claim 1, characterized in that the crystallization as per step b) or c) takes place at temperatures of −50 to 80° C.

4. The process of claim 1, characterized in that the distillate from step b) or the residue from step a) is admixed with water.

5. The process of claim 1, characterized in that the distillate from step b) or the residue from step a) is admixed with crystalline 4-isopropyl-3-methylphenol.

6. The process of claim 1, characterized in that the crystallization takes place as a result of cooling.

7. The process of claim 6, characterized in that the cooling takes place in a tube, tube bundle or container coolable by means of other internals, this apparatus being cooled in comparison to the ambient temperature, and the resultant crystals, after the other compounds have been drained off, are melted off by heating of the tube, tube bundle or container coolable by other internals.

\* \* \* \* \*